US012036358B2

(12) United States Patent
Kulkarni et al.

(10) Patent No.: US 12,036,358 B2
(45) Date of Patent: Jul. 16, 2024

(54) SINGLE BLISTER-STRIP BASED DISPENSER

(71) Applicant: CIPLA LIMITED, Mumbai (IN)

(72) Inventors: Nandan Kulkarni, Maharashtra (IN);
Pavan Shewale, Maharashtra (IN);
Geena Malhotra, Maharashtra (IN)

(73) Assignee: CIPLA LIMITED, Mumbai (IN)

( * ) Notice: Subject to any disclaimer, the term of this patent is extended or adjusted under 35 U.S.C. 154(b) by 689 days.

(21) Appl. No.: 17/274,715

(22) PCT Filed: Sep. 9, 2019

(86) PCT No.: PCT/IN2019/050649
§ 371 (c)(1),
(2) Date: Mar. 9, 2021

(87) PCT Pub. No.: WO2020/053878
PCT Pub. Date: Mar. 19, 2020

(65) Prior Publication Data
US 2021/0346619 A1     Nov. 11, 2021

(30) Foreign Application Priority Data
Sep. 10, 2018   (IN) .............................. 201821034038

(51) Int. Cl.
*A61M 15/00*   (2006.01)
(52) U.S. Cl.
CPC .... *A61M 15/0051* (2014.02); *A61M 15/0003* (2014.02); *A61M 15/0026* (2014.02);
(Continued)
(58) Field of Classification Search
CPC .......... A61M 15/0001; A61M 15/0021; A61M 15/0023–0026; A61M 15/0028;
(Continued)

(56) References Cited

U.S. PATENT DOCUMENTS 5,575,280 A    11/1996  Gupte et al.
8,474,448 B2    7/2013  Oi et al.
(Continued)

FOREIGN PATENT DOCUMENTS

CA    2578812 A1    2/2004
CA    2681299 A1    9/2008
(Continued)

OTHER PUBLICATIONS

GCC Patent Office Examination Report for Application No. GC 2019-38257; Filing Date—Sep. 10, 2019; dated Jun. 18, 2021, 3 pages.
(Continued)

*Primary Examiner* — Valerie L Woodward
*Assistant Examiner* — Paige Kathleen Bugg
(74) *Attorney, Agent, or Firm* — CANTOR COLBURN LLP (57) ABSTRACT

The present subject matter refers a blister-strip based dispenser (100) comprising a lever arm rotatable on receiving a user-actuation. A chassis (106, 108) is provided for supporting placement of at least one blister-strip (104) in the form of the coil. The blister-strip (104) comprises medicament-pockets at at-least one side of the blister-strip (104). A plurality of interconnected-rollers (110, 114, 116) comprises at-least one roller linked to the lever-arm and rotatable by the lever arm. The plurality of interconnected rollers (110, 114, 116) are configured for anchoring the blister-strip (104) from one end for enabling the placement in a coil-form and unwinding of the blister strip (104) from the coil-form, guiding at least two split-portions of the blister-strip (104), anchoring an end of each of said at-least two portions of the blister-strip (104) for winding the at-least two portions separately, and anchoring an end of a lid-foil peeled off the at least two portions for winding the lid-foil.

12 Claims, 10 Drawing Sheets

(52) U.S. Cl.
    CPC .... *A61M 15/0043* (2014.02); *A61M 15/0055* (2014.02); *A61M 15/0075* (2014.02); *A61M 2202/064* (2013.01)

(58) Field of Classification Search
    CPC .......... A61M 15/0031; A61M 15/0043; A61M 15/0045; A61M 15/0051; A61M 15/0053–0055; A61M 15/0061–0063
    USPC .................................................... 128/203.15
    See application file for complete search history.

(56) References Cited

U.S. PATENT DOCUMENTS

| | | | |
|---|---|---|---|
| 8,567,394 B2 | 10/2013 | Herder et al. | |
| 2005/0005934 A1* | 1/2005 | Harvey | A61M 15/008 128/203.15 |
| 2005/0183723 A1 | 8/2005 | Pinon et al. | |
| 2005/0268909 A1* | 12/2005 | Bonney | A61M 15/0043 128/203.15 |
| 2006/0196504 A1 | 9/2006 | Augustyn et al. | |
| 2008/0196718 A1 | 8/2008 | Connell et al. | |
| 2009/0139516 A1 | 6/2009 | Augustyn et al. | |
| 2011/0253139 A1 | 10/2011 | Guthrie et al. | |
| 2012/0132203 A1 | 5/2012 | Hodson et al. | |
| 2016/0022933 A1 | 1/2016 | Ciancone et al. | |
| 2016/0051776 A1 | 2/2016 | Von Hollen | |
| 2016/0144141 A1 | 5/2016 | Biswas et al. | |
| 2019/0070371 A1 | 3/2019 | Von Schuckmann | |

FOREIGN PATENT DOCUMENTS

| | | | |
|---|---|---|---|
| GB | 2242134 A | 9/1991 | |
| WO | 1992009322 A1 | 6/1992 | |
| WO | 03061743 A1 | 7/2003 | |
| WO | 2005014089 A1 | 2/2005 | |
| WO | 2009003989 A1 | 1/2009 | |
| WO | 2017051389 A1 | 3/2017 | |
| WO | WO-2020025977 A1 * | 2/2020 | ............ A61M 11/00 |

OTHER PUBLICATIONS

International Search Report; International Application No. PCT/IN2019/050649; International Filing Date—Sep. 9, 2019; dated Jan. 24, 2020; 2 pages.
Written Opinion; International Application No. PCT/IN2019/050649; International Filing Date—Sep. 9, 2019; dated Jan. 24, 2020; 6 pages.

* cited by examiner

SINGLE BLISTER-STRIP BASED DISPENSER

CROSS REFERENCE TO RELATED APPLICATIONS

This application is a National Stage application of PCT/IN2019/050649, filed Sep. 9, 2019 which claims priority to Indian Application No. 201821034038, filed Sep. 10, 2018 and all the benefits accruing therefrom under 35 U.S.C. § 119, the content of which is incorporated by reference in its entirety.

FIELD OF THE INVENTION

The present disclosure relates to dry power inhalers (DPI) for delivering drugs in a solid dry powder form and in particular relates to inhalers based on powdered-drug packed in blisters.

BACKGROUND

Inhalation provides several advantages over delivery-techniques such as oral delivery via the mouth or intravenous delivery using a syringe. Inhalation is fast, patient-friendly, non-invasive, and provides rapid-absorption into the body.

Inhalers as device are used to deliver drugs into patient's-lungs through inhalation which could be either in the form of dry powder inhaler (DPI) or metered dose inhaler (MDI). Typically, an inhaler contains or provides a mixture of one or more drugs and air with either powdered excipients (in case of DPIs) or propellants (in case of MDIs). The mixture is delivered via the patient inhaling from a mouthpiece on the inhaler, for treatment of various conditions, for example, bronchial-asthma and/or chronic obstructive pulmonary disease (COPD).

In case of DPI devices, blister-packs are known to store pre-measured amounts of powdered medicament in separate-pockets. The usage of blister-packs (typically with 30 or 60 pockets) in inhalers to dispense powder of pre-determined amounts as a part of single dose is known. Unlike unit-dose inhalers which use a capsule filled with powder or a single blister pocket each time a dose has to be taken, blister-based inhalers are multi-dose inhalers having multiple blister-pockets. For example, Patent publication GB2242134 describes a device which uses a flexible strip defining a plurality of pockets each of which contains a dose of medicament which can be inhaled. The device contains a chamber in which the strip is housed, an opening station which comprises means for peeling the strip apart into two-sheets, and finally an outlet through which the user can inhale the medicament.

The aforesaid multidose-dose inhalers are useful for rendering single dose treatments, non-chronic applications, controlled or very expensive drugs where large quantities of drug would not be acceptable, or for drugs where overdose or abuse would have serious consequences. The multi-dose inhalers may also be advantageous for children where providing them with a single dose only avoids the potential for overdosing.

Figure 1:
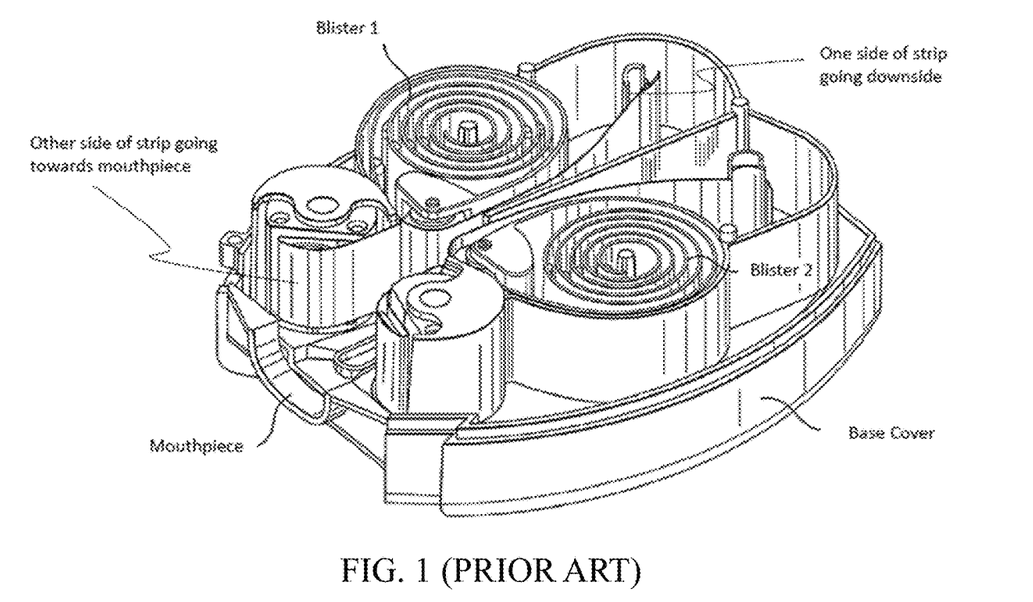
FIG. 1 illustrates a prior art multi-dose inhaler.
Figure 2A:
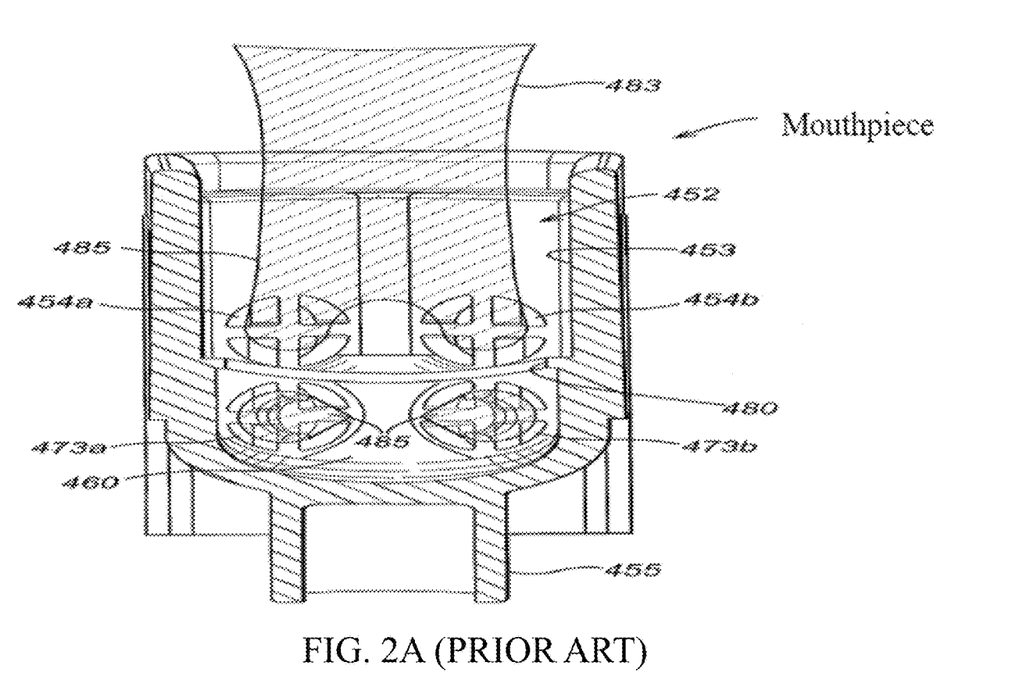
FIG. 2 illustrates a sectional view of the aforesaid prior art multi-dose inhaler.
Figure 2B:
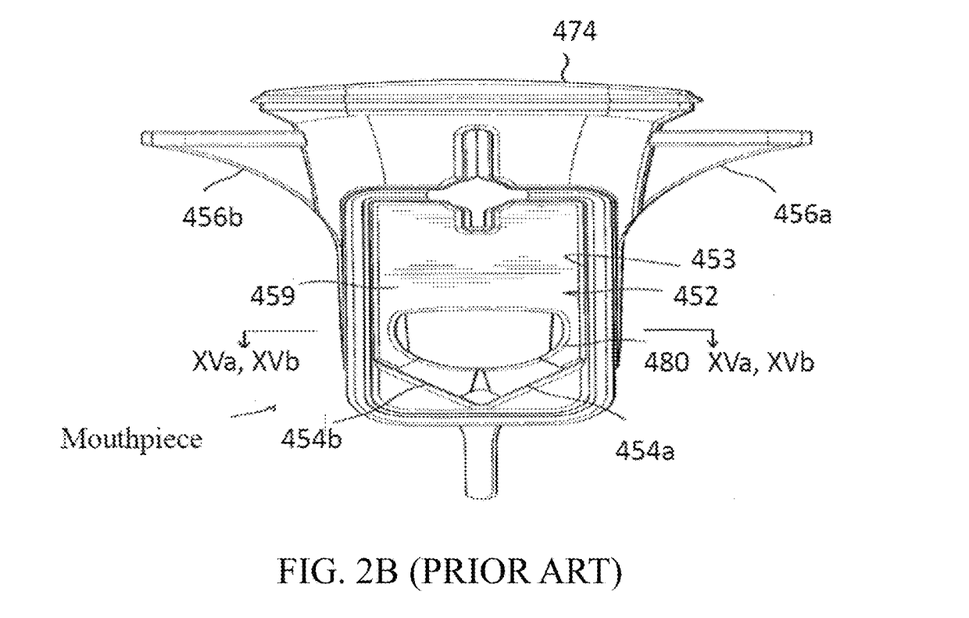

Another example prior art DPI or multi-dose inhaler is shown in FIG. 1 and FIG. 2. As indicated in FIG. 1, a plural blister arrangement has been shown, wherein two blister strips are placed as referred by Blister 1 and Blister 2. Said two strips comprise different-medication and are peeled separately through using separate unwinding-mechanisms. One side of strip which has blister cavity goes towards downside of device and other side of strip is wound by using separate winding mechanism towards mouthpiece side.

However, for the device as shown in FIG. 1, in case a single medication is to be dispensed, one blister strip area (e.g. either Blister 1 or Blister 2) is required to be kept vacant. Moreover, the device of FIG. 1 is unable dispense more than two medicines/drugs as a part of single dose, unless one of the blister-strip adopts a fixed dose combination of 2 active drugs. Accordingly, in case dispensation of more than two type of drugs is required as a part of single dose, the same entails implementing two carefully-chosen dissimilar blister-strips. In absence of the same, an overhaul with respect to the device of FIG. 1 is required, e.g. change of the form-factor and footprint/layout of the device. Overall, the device of FIG. 1 necessitates separate blister strip for each medication, which in turn entails separate manufacturing, assembly and testing for the plural blisters.

Further, a mouthpiece with respect to the device of FIG. 1 has been depicted in FIG. 2a and FIG. 2b. Said mouthpieces exhibit structural limitations in terms of dispensation of drugs as a part of single-dose. In an example, the mouthpiece renders achievement of an insufficient mixing of drugs during the inhalation.

Still further, many a times a user misses inhaling a dose despite having triggered the dispenser for the same. Within the prior art inhalers (including as depicted above), the non-inhaled or waste-dose remains present inside the peeled open blister cavity or gets dispersed across the chassis of the device. Accumulation of waste dose is known to potentially cause change in device functioning, at least by dose-contamination or dis-proportioning of next dose. In the worst case scenario, it may altogether jam the machinery of the device and lead to breakdown.

Accordingly, there remains a long-felt need to provide an improved dry power inhaler operating upon the blister-packs.

SUMMARY

This summary is provided to introduce a selection of concepts in a simplified format that are further described in the detailed description of the present disclosure. This summary is neither intended to identify key or essential inventive concepts of the disclosure, nor is it intended for determining the scope of the invention or disclosure.

At-least in order to obviate the aforesaid drawbacks of the conventional dry powder inhaler (DPI), the present subject matter is related to a dispensing device that at least facilitates dispensation of a plurality of type of medicaments (i.e. two or more type of drugs) through employment of a single blister-strip and thereby avoids a complex arrangement otherwise needed for operating upon plurality of individual strips. Furthermore, the present subject matter renders a provision wherein waste-dose is collected comprehensively as a part of device-mechanism and isolated from the dispensing mechanism of the blister to prevent cross-contamination and mal-functionality of device due to waste-dose accumulation The present subject matter refers a blister-strip based dispenser which comprises:
- a lever arm rotatable on receiving a user-actuation,
- a chassis provided for supporting placement of at least one blister-strip in the form of the coil, such that the blister-strip comprises medicament-pockets at at-least one side of the blister-strip, and a plurality of interconnected-rollers comprising at-least one roller linked to the lever-arm and rotatable by the lever arm, wherein such plurality of interconnected rollers are configured for:
  anchoring the blister-strip from one end for enabling the placement in a coil form and unwinding of the blister strip from the coil form,
  guiding at least two split-portions of the blister-strip, anchoring an end of each of said at least two portions of the blister-strip for winding the at least two portions separately, and
  anchoring an end of a lid-foil peeled off the at least two portions for winding the lid-foil.

In an implementation, the dispenser comprises a waste-dose collection mechanism for collecting the non-inhaled medicament from peeled blister-strip ends in a designated chamber.

In an implementation, the waste-dose collection mechanism comprises two open-ended funnels placed over slotted gears to collect the non-inhaled medicament upon alignment of the funnel with the slot in the gear.

In an implementation, the driving mechanism drives the plurality of rollers through a train of gears.

At least by virtue of aforesaid features, the present subject matter employs a single-blister containing plural medications that can deliver the said medication as combination or individually. The waste-dose collector ensures that the non-inhaled medicament present in the peeled of blister strip neither falls out of device, nor interferes with the working, and resides securely inside the designated waste dose collection chamber.

Furthermore, a dose counter is provided which counts each dose individually and provides a visual-indication for the remaining doses in the medication dispenser.

To further clarify advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 6 (as 6a and 6b) illustrates schematic views of a single blister-strip for the device of FIG. 3, in accordance with an embodiment of the present invention.

FIG. 7 (as 7a and 7b) illustrates schematic views of another blister-strip for the device of FIG. 3, in accordance with an embodiment of the present invention.

FIG. 9 (as 9a and 9b) illustrates a mouthpiece for the device of FIG. 3, in accordance with an embodiment of the present invention.

The elements in the drawings are illustrated for simplicity and may not have been necessarily been drawn to scale. Furthermore, in terms of the construction of the device, one or more components of the device may have been represented in the drawings by conventional symbols, and the drawings may show only those specific details that are pertinent to understanding the embodiments of the present disclosure so as not to obscure the drawings with details that will be readily apparent to those of ordinary skill in the art having benefit of the description herein.

DETAILED DESCRIPTION OF FIGURES

For the purpose of promoting an understanding of the principles of the present disclosure, reference will now be made to the embodiment illustrated in the drawings and specific language will be used to describe the same. It will nevertheless be understood that no limitation of the scope of the present disclosure is thereby intended, such alterations and further modifications in the illustrated system, and such further applications of the principles of the present disclosure as illustrated therein being contemplated as would normally occur to one skilled in the art to which the present disclosure relates.

Reference throughout this specification to "an aspect", "another aspect" or similar language means that a particular feature, structure, or characteristic described in connection with the embodiment is included in at least one embodiment of the present disclosure. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Unless otherwise defined, all technical and scientific terms used herein have the same meaning as commonly understood by one of ordinary-skill in the art to which this present disclosure belongs. The system, methods, and examples provided herein are illustrative only and not intended to be limiting.

Embodiments of the present disclosure will be described below in detail with reference to the accompanying drawings.

Figure 3:
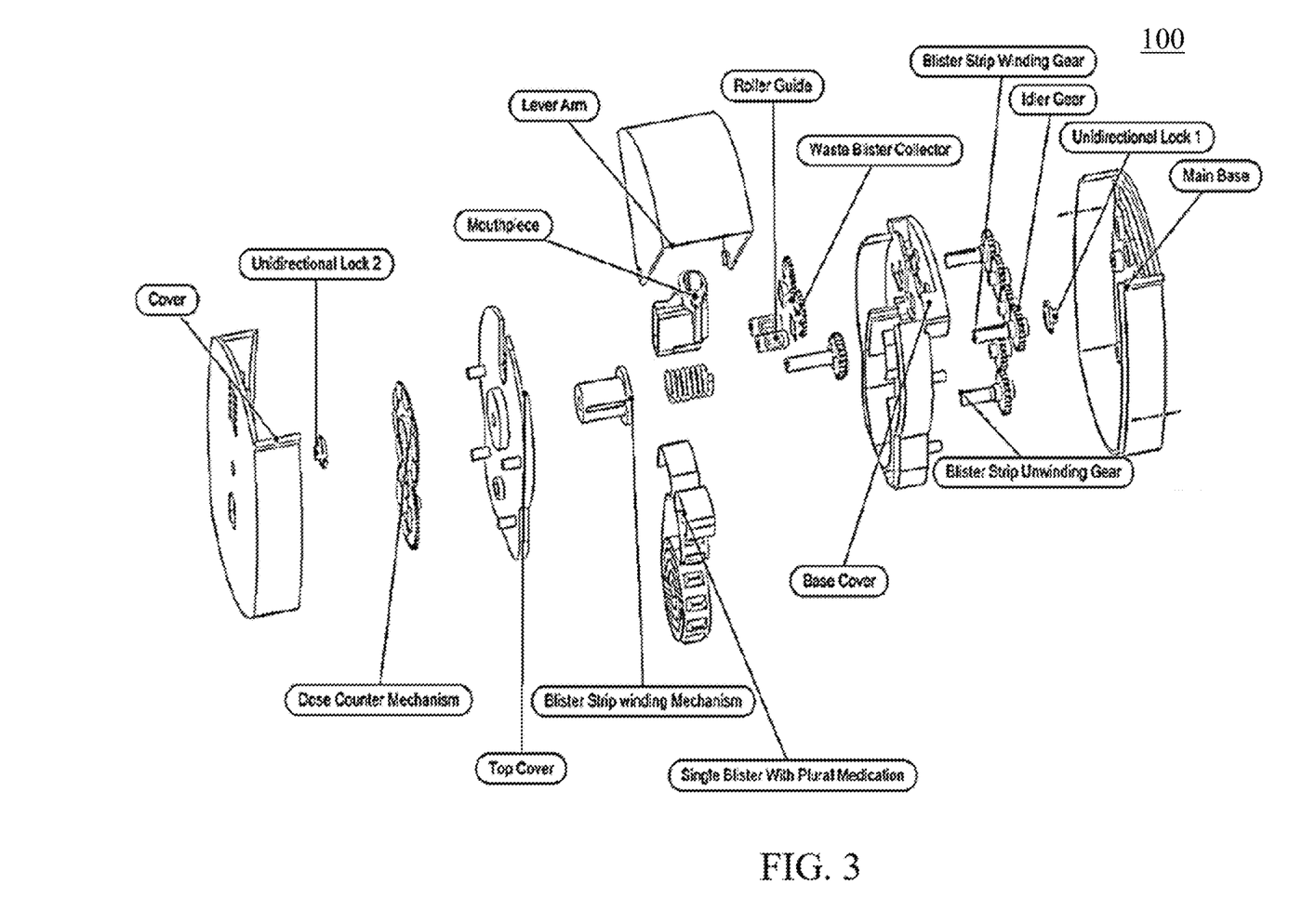
FIG. 3 illustrates an exploded view a blister-strip based dispensing device, in accordance with an embodiment of the present invention.

FIG. 3 illustrates an exploded view of a blister-strip based dispenser 100 or a blister-strip based dispensing device 100, in accordance with an embodiment of the present invention. As indicated in the figure, the dispensing device 100 is an assembly of cover, top cover, base cover and main base that collectively represent the housing of the dispenser 100.

The space enclosed between cover and top cover comprises the counter for counting the number of doses. In addition, a unidirectional-lock ensures the rotation in single direction.

The top cover and base cover enclose a blister-pack assembly and a lever arm, which is a movable-cover covering the mouthpiece. The lever-arm is rotatable on receiving a user-actuation. In an example, the user-actuation to the lever-arm may be a pull imparted to the lever-arm to open it from closed-state and a push imparted to close the lever arm from the open state. The push/pull as subjected may cause the lever arm to undergo a circular, elliptical, parabolic or any other type of analogous motion. The lever arm moves the main gear in the device and triggers rotary motion. In addition, a waste-dose collection mechanism is implemented therein to collect waste or non-inhaled medicaments from the blister-pack.

The base-cover and main base enclose a gear-train (e.g. a planetary gear system) provided for transferring the rotary motion from the motion-source in the device. In addition, a mechanical/electro-mechanical counter is provided to count the number of doses. Also attached is another uni-directional lock for ensuring the movement of the main driving-gear within the gear-train in a single-direction only.

Figure 4:
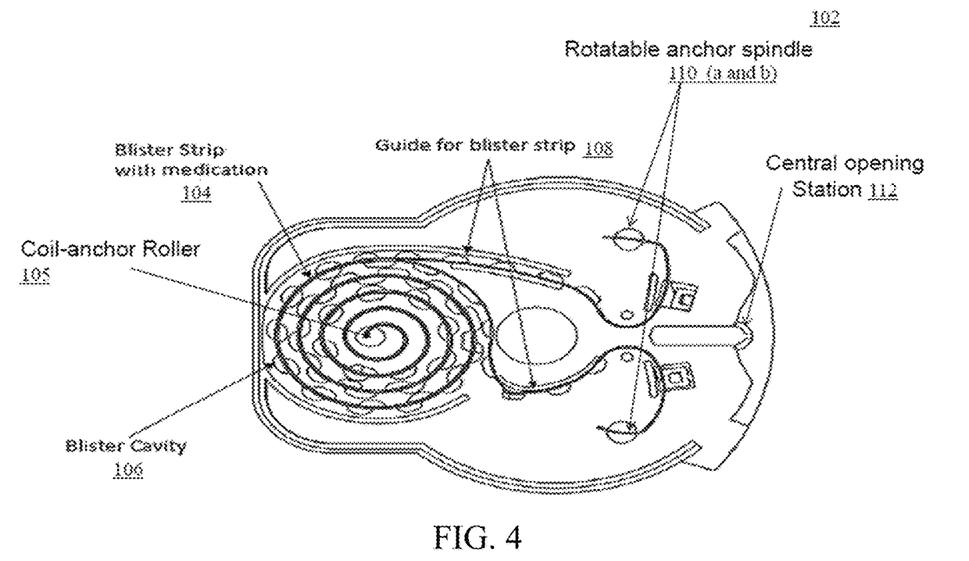
FIG. 4 illustrates a top-view of the blister pack assembly of the device of FIG. 3, in accordance with an embodiment of the present invention.
Figure 5:
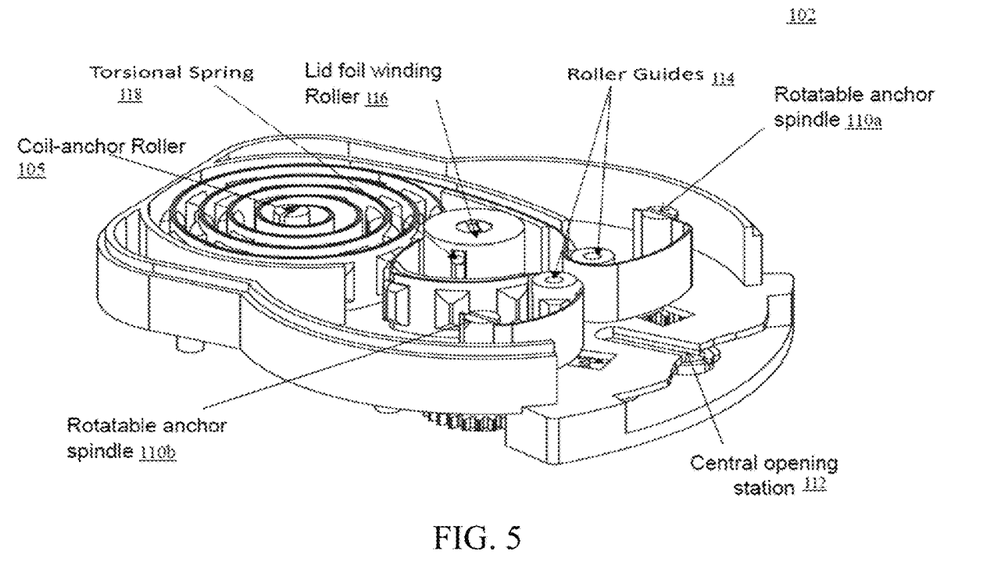
FIG. 5 illustrates an isometric view of the blister pack assembly of the device of FIG. 3, in accordance with an embodiment of the present invention.

FIGS. 4 and 5 illustrates top and isometric views of the base-cover 102 of the device 100 of FIG. 3, wherein the base-cover 102 of the device 100 supports the blister-pack assembly and ancillary-components and forms a part of the housing of the device 100.

A 'Single' blister-strip 104 containing first and second medicaments (as later referred in FIG. 6 and FIG. 7) are positioned within a blister-cavity 106 of the base cover 102. Specifically, a roller 105 is adapted for anchoring the blister-strip 104 from one end and may be referred as a coil-anchor roller 105. The coil-anchor roller 105 enables the placement of the blister-strip 104 in the coil-form. Moreover, the roller 105 is configured to roll or rotate for facilitating unwinding of the blister strip 104 from the coil-form upon rotation. Accordingly, a combination of the roller 105 along with a blister-strip unwinding gear 806 constitute 'a blister strip unwinding mechanism', wherein the blister-strip unwinding gear 806 is later shown in FIG. 8.

In addition, the chassis of dispenser 100 also contributes to such maintenance of the blister strip 104 in the coil form. The chassis corresponds to the specific internal-structure within the housing of the dispenser 100 to aid such maintenance in the coil-form and is defined by co-presence of a plurality of guide-walls 108 referred as 'guide for blister strip' (shown in FIG. 4) and a cavity 106 within the dispenser 100.

The split-ends or the split portions of the single blister-strip 104 (when the blister strip 104 is unwound) are guided by the 'guide for blister strip' 108 (shown in FIG. 4) and are finally anchored in respective 'rotatable anchor spindle' 110a and 110b (shown in FIG. 4 and FIG. 5). Such rotatable anchor spindles 110a and 110b may be defined by a pair of rollers 110 that are adapted for anchoring the end of each of the two split-portions of the blister-strip 104 for winding the two split portions separately.

Figure 9A:
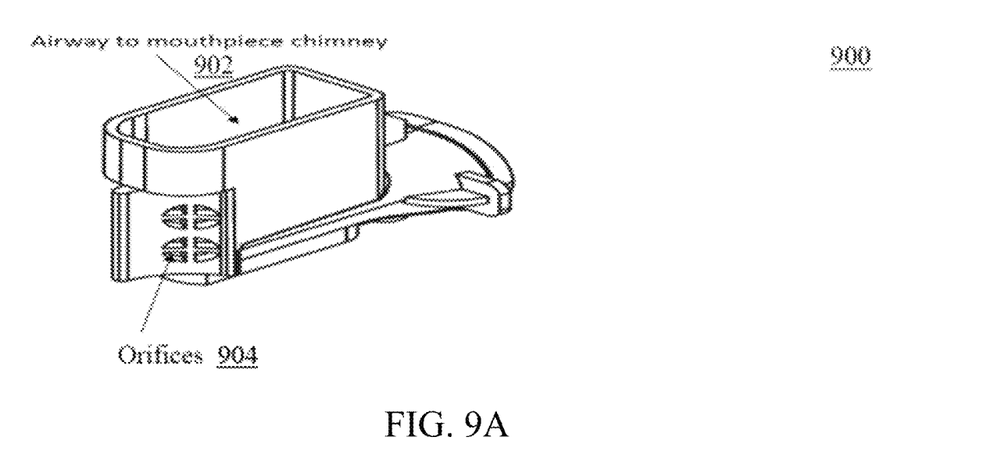

More specifically, each of the rotatable anchor spindle 110 anchors the end of each respective portion of the blister-strip 104 and accordingly winds each portion of the blister-strip 104 as the coil. The anchor spindles 110 are coupled together and rotate in unison, though in opposite-directions. Further, successive pockets within each split-portion of the blister-strip 104 are thereby guided towards a central-opening station 112 that receives a mouthpiece (shown later in FIG. 9).

At the central opening station 112, a lid foil part of each split portion of the blister strip 104 is peelably separable about beak or roller-guides 114 (as shown in FIG. 5). The resulting blister-strip portion without lid-foil or waste-blisters coils up in respective rotatable anchor-spindle 110. Progressive rotation of each respective anchor spindle 110 results in the 'waste' blister-strip being wound up there around into a tight coil.

Typically, the rotation of each anchor spindle 110 triggers the movement of the split portions of the blister-strip 104 towards the anchor spindle 110, which in turn triggers rotation of respective roller guide 114. The roller guide 114 is a roller-bearing for contacting the at-least two portions of the blister strip 104 and is rotatable upon having been subjected to a drag generated by a movement of the split-portions of the blister-strip 104 towards the corresponding anchor spindle 110.

The waste lid-foil feeds over its respective roller guide 114 and coils about a common lid-foil winding mechanism (or a blister-strip winding mechanism) 116 connected to a main driving-gear of the device 100 in the gear train. The common lid-foil winding mechanism may be interchangeably referred as a lid-foil winding roller 116 or a lid-foil take up spindle 116 which is adapted for anchoring an end of the lid-foil and winding the lid-foil upon rotation.

The lid foil take-up spindle 116 is provided with a centrally-located torsion spring 118. The function of the torsion spring 118 is to ensure a roughly constant driving tension is provided to each split portion of the blister strip 104 by the lid take-up spindle 116 over the course of entire strip length with respect to each split end of the blister-strip 104. In particular, the torsion spring 118 acts to compensate for the variation in drive tension associated with the increase in the effective winding diameter of the lid take-up spindle 116 as used lid foils gradually becomes wrapped there around. Thus, a uniform indexing of each split blister-strip 104 is maintained over the entire strip length.

In operation, the dispensing device 100 is primed by a user-actuation of the lever-arm. The lever arm is pivoted within the housing of the dispenser 100 for covering the mouthpiece in closed-state, wherein said mouthpiece has been later shown in FIG. 9. The lever arm covers the central opening station 112 in closed-state. Further, the open state of the lever arm exposes the mouthpiece and the central opening station 112. Such transition from close to open state and vice-versa is triggered by the user-actuation imparted by the lever-arm.

The lever arm directly rotates the main driving gear which is connected to the lid-foil take up spindle 116 or the lid foil winding roller 116. Said main driving gear has been referred as 'driving gear 802' in FIG. 8. The main driving gear in turn rotates the two rotatable anchor-spindles 110 anchoring the ends of the split-portions of the blister strip 104. Accordingly, each split-portion of the blister strip 104 is advanced or moved towards the anchor spindles 110, thereby causing a leading pocket in each end of the blister-strip 104 to be peeled open. To access the contents of the opened-pockets, the patient then breathes in through an outlet defined by the mouthpiece. This results in negative-pressure being transmitted to the opened leading-pocket of each end of the blister strip 104 at the mouthpiece. In turn, the medicament-powder contained within each of the opened pockets is drawn towards the mouthpiece, thereby enabling the patient to inhale combination of medicament dose from each end of the blister-strip 104. As may be understood, mixing of each separately delivered component of the combined medicament product happens as the powder is transported from each opened pocket towards the outlet.

Figure 6A:
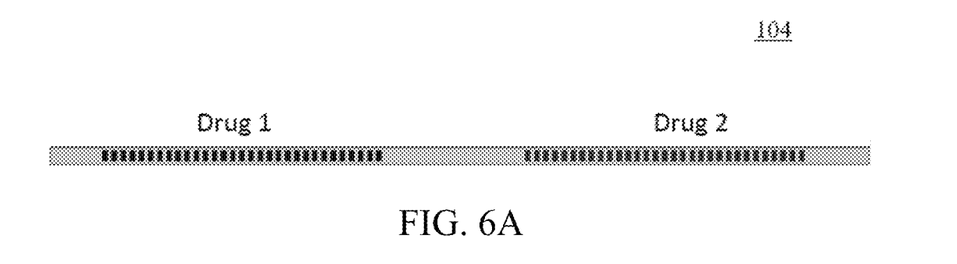
Figure 6B:
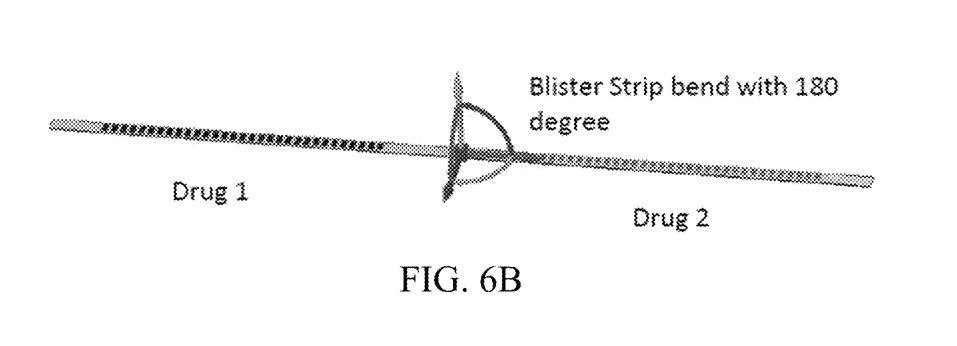

FIG. 6 (a and b) illustrates a medicament-carrier 104 or blister-strip 104 suitable for use in accordance with the present invention.

As may be understood, the medicament carrier 104 comprises a flexible-strip defining a plurality of pockets each of which contains a portion of a dose of medicament of a form suitable for inhalation and in the form of powder. The strip 104 comprises a base sheet in which blisters are formed to define the pockets and a lid sheet which is hermetically sealed to the base sheet except in the region of the blisters in such a manner that the lid sheet and the base sheet can be peeled apart.

In an example, the lid and base-sheets are sealed to one another over their whole width except for the leading end portions where they are preferably not sealed to one another at all. The lid and base sheets are each formed of a plastics/aluminium laminate and are suitably adhered to one another by heat sealing. The lid sheet comprises at least the following successive layers: (a) paper; adhesively bonded to (b) polyester; adhesively bonded to (c) aluminium foil; that is coated with a heat seal lacquer for bonding to the base sheet. The base sheet comprises at least the following successive layers: (a) oriented polyamide (OPA); adhesively bonded to (b) aluminium foil; adhesively bonded to (c) a third layer comprising a polymeric material (e.g. polyvinyl chloride).

At least in accordance with the present invention, the single blister-strip 104 employs single or plurality of types of medicaments. FIG. 6a illustrates single blister strip 104 as containing two different types of drugs (Drug 1 and Drug 2). The inter-pocket spacing in respect of Drug 1 and Drug 2 may be pre-determined so as to cause a synchronized inhalation of Drug 1 and Drug 2, once the lid foil has been peeled off. In other example, the Drug 1 and Drug 2 may also be placed on the opposite sides of the strip, instead of being placed on the same side as shown in FIG. 6a.

In yet other example, the blister-strip 104 may only comprise a single-type of drug instead of different types of drug. Accordingly, the representation in FIG. 6a may be construed to cover the blister strip 104 having a single type of drug, for example "Drug 1" only.

As shown in FIG. 6b the blister-strip 104 may be folded halfway or at the centre to produce back-to-back placed medicament pockets in blister-strips 104a and 104b for the purposes of packing within the blister-cavity 106 in the form of coil (as shown in FIG. 4 and FIG. 5). However, alternatively, identically-sized blister strips may be loosely pasted back to back to achieve a single blister strip 104, such that the same has an ease of separation into two blister-strips 104a, 104b as needed by the present dispenser device 100.

Figure 7A:
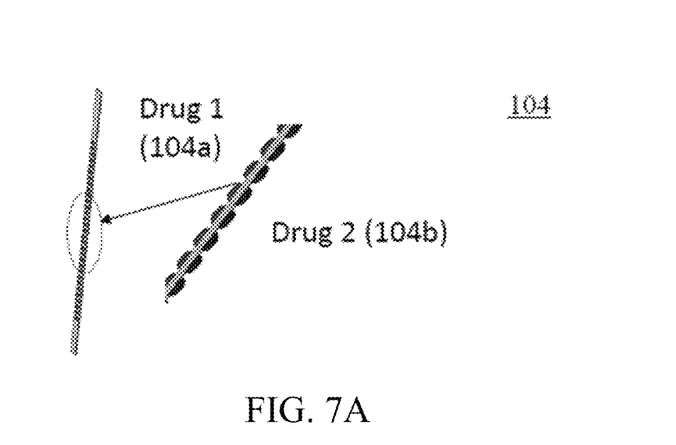
Figure 7B:
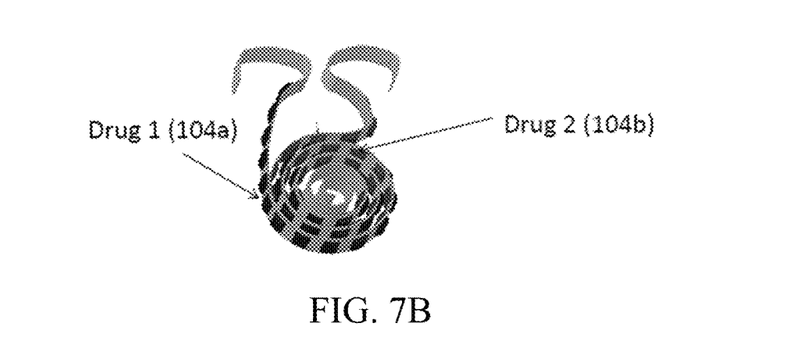

FIG. 7a depicts the folded blister strip 104 of FIG. 6a, and thereby depicting back to back placed medicament pockets in the single blister-strip 104. FIG. 7b depicts the coiled shape of the blister strip of FIG. 7a meant for incorporation within the base cover 102 in FIG. 3-5. More specifically, the unified-end of the blister strip 104 is anchored to the coil-anchor roller 105 which in turn is connected to the blister-strip unwinding gear 806 (shown in FIG. 8) within the gear-train.

In an example, two blister-strip based coils 104 may be provided within the cavity 106 of the base cover 102 in a 'double decker' arrangement, i.e. one over another. Accordingly, the device is scalable to increase the number of doses (e.g. more than 2 type of drugs) that can be delivered without changing the form factor. In an example, more than three types of medicament may be dispensed for inhalation through the present device simultaneously, without requiring any structural modification.

Figure 8:
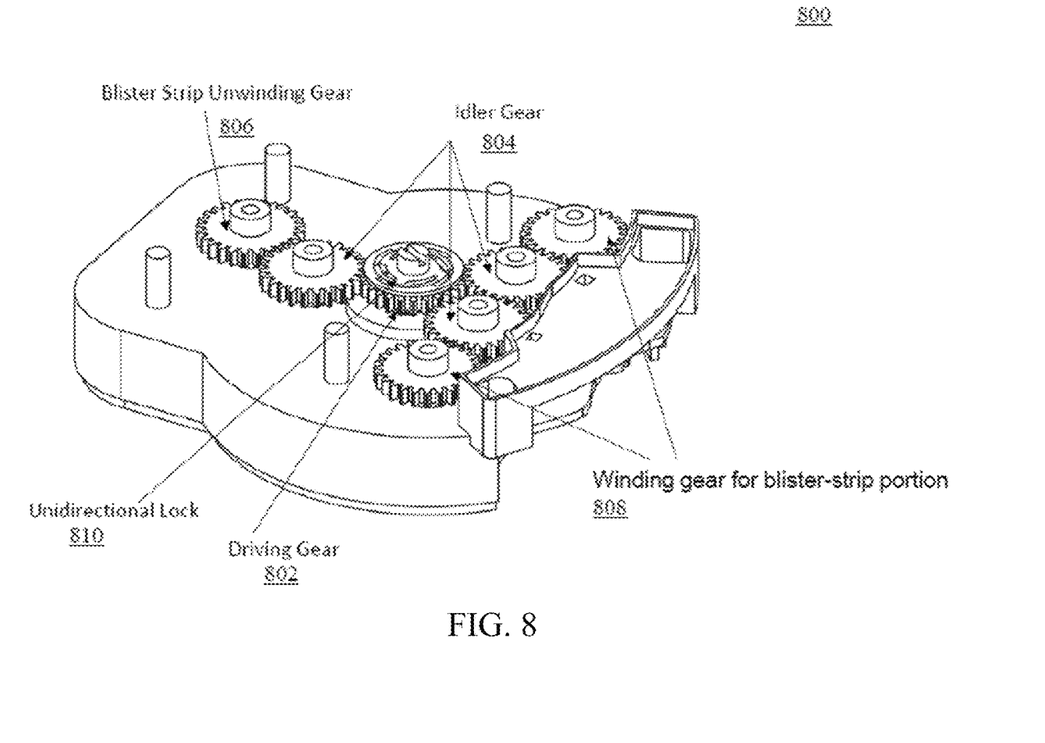
FIG. 8 illustrates a gear-train assembly for the device of FIG. 3, in accordance with an embodiment of the present invention.

FIG. 8 illustrates a gear-train assembly 800 for the device of FIG. 3, in accordance with an embodiment of the present invention. In an implementation, the assembly 800 is a planetary-gear system 800 comprising a driving gear 802 driven by the lever-arm. As indicated in FIG. 3, the gear train assembly 800 is provided between the base-cover 102 and main-base, and comprises a main driving gear 802. The driving gear 802 is connected to the lever arm and supports the lid-foil winding roller 116 adapted for anchoring an end of the lid-foil and winding the lid-foil upon rotation;

Further, the assembly 800 comprises a set of idler gears 804, a blister strip unwinding gear 806 and a pair of blister strip winding gears 808. Specifically, the gears 806, 808 correspond to driven gears 806, 808 by the driving gear 802 for winding the at least two portions of the blister-strip 104 and unwinding the blister-strip 104. For such purpose, the driven gear 806 supports the roller 105 as adapted for anchoring the blister-strip 104 from one end for enabling the placement in the coil form and for unwinding the blister strip 104 from the coil-form upon rotation. The other driven gear 808 or the pair of driven gears 808 support the rotatable anchor-spindle 110 and is adapted for anchoring the end of each of two portions of the blister-strip 104 for winding the two portions of the blister strip 104 separately.

Further, a unidirectional lock 810 is provided to ensure rotation of the driving gear 802 in a specified direction only.

As may be understood, in operation, the actuation of the lever arm leads to rotary-motion of the driving-gear 802, which causes motion of blister-strip unwinding gears 806 and blister strip winding-gears 808. In addition, a lid foil winding drum acting as the lid foil winding roller 116 is attached to the driving gear 802 and rotates to peel off the lid foil and thereby wraps the peeled off lid foil around itself.

Overall, the present assembly 800 or the planetary gear system 800 leads to an interconnection among the rotatable anchor spindle 110, the roller guides 114 and lid-foil take up spindle 116. In other words, the rotatable anchor spindle 110, the roller guides 114 and lid-foil take up spindle 116 collectively represent a plurality of interconnected rollers 110, 114, 116 wherein the lid-foil take up spindle 116 is directly linked to the lever arm and rotatable by the lever arm. As may be understood such plurality of interconnected rollers 110, 114, 116 upon rotation are operable to unwind the blister strip 104 from the coil form, guide the two split-portions of the blister-strip 104 to the corresponding anchor spindle 110 for winding, winding the two portions of the blister strip 104 separately, and winding the lid-foil peeled off the two portions.

Figure 9B:
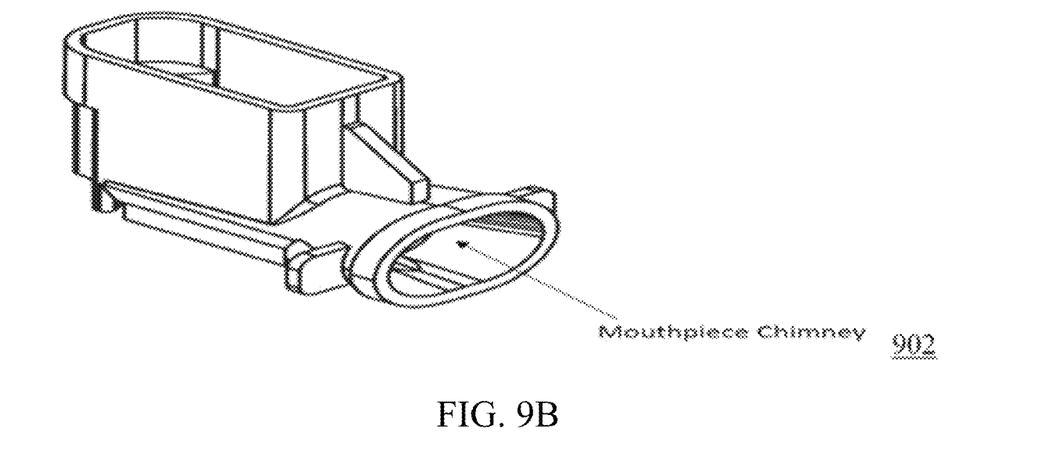

FIG. 9 illustrates a mouthpiece 900 for the device of FIG. 3, in accordance with an embodiment of the present invention. As may be observed, the mouthpiece 900 rendered by the present device provides a right mixing of plurality of medications. More specifically, the mouthpiece 900 facilitates a right combination of mixing guide plane, chimney 902 and orifice 904 that delivers the plural medication as a combination and helps appropriate mixing of these medicaments to provide required dose parameters.

Figure 10:
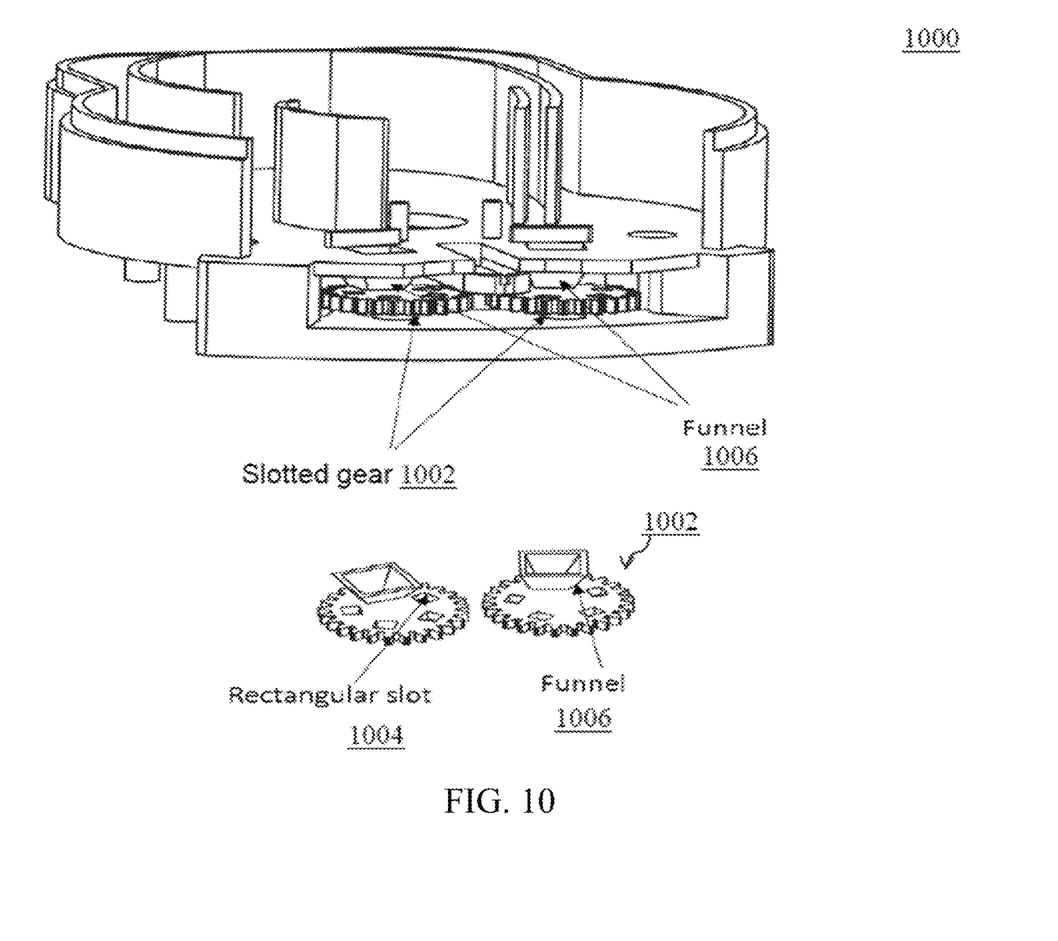
FIG. 10 illustrates a collection mechanism for non-inhaled medicament in the device of FIG. 3, in accordance with an embodiment of the present invention.

FIG. 10 illustrates a waste-dose collection mechanism 1000 for non-inhaled medicament or waste blisters in the device of FIG. 3, in accordance with an embodiment of the present invention. The waste dose collector arrangement is used to collect any medication which may be actuated by the operating lever arm, not consumed or inhaled, and remains inside the device 100. The waste-dose collection mechanism comprises two waste dose collector gears 1002 or slotted gears 1002 defining plurality of rectangular-slots 1004 or gear slots 1004 of defined dimensions. In such a manner, the orientation of the device 100 (upright, tilted or any angle of operation) does not interfere in the gear-slot mechanism.

In operation, funnel 1006 opens to waste dose collector when the gear slot 1004 vertically aligns with the funnel opening. Such alignment is met only when the lever-arm is rotated for medication. During the reverse rotation of lever arm for restoring the open lever-arm to "rest condition" or during regular-inhalation when the lever arm is at completely open position, the waste dose collector funnel 1006 remains non-aligned with slots 1004 on the gear 1002, thereby ensuring that waste dose does not get introduced into inhaled air. Further, the waste dose collector 1000 is designed with a capacity to accommodate all 100% available doses in the device.

Figure 11:
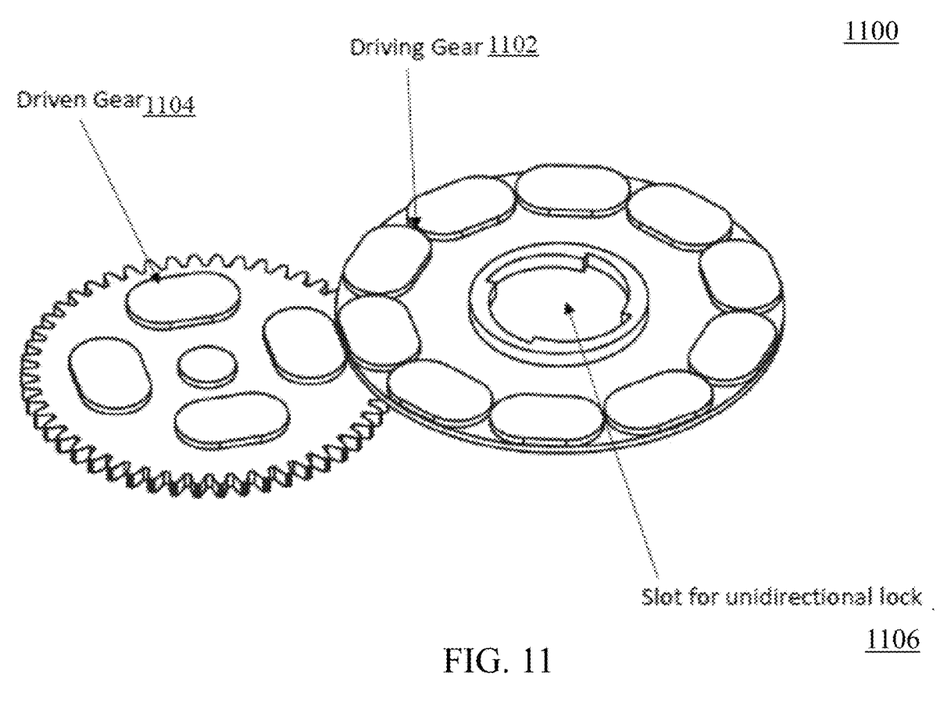
FIG. 11 illustrates a dose-counter mechanism in the device of FIG. 3, in accordance with an embodiment of the present invention.

FIG. 11 illustrates a dose-counter mechanism 1100 in the device of FIG. 3, in accordance with an embodiment of the present invention. The dose-counter mechanism comprises two gears one driving 1102 and other driven 1104. The driving gear 1102 has a slot for unidirectional lock. The arrangement is made such that one complete rotation of driving gear 1102 will rotate driven gear 1104 to a quarter of the rotation of driven gear 1104.

At least by virtue of aforesaid features, the present subject matter at least renders a Single blister containing plural medication that can deliver the said medication as combination or individually.

Further, a waste dose collector ensures that upon using dispenser but not inhaling the medication through it, the medication does not fall out of device or interferes with the working of device subsequently and resides securely inside the waste dose collection chamber till the working life of the device.

Furthermore, the present subject matter illustrates the mouthpiece for right mixing of plural medications—a right combination of mixing guide plane, chimney and orifice that delivers the plural medication as combination and helps appropriate mixing of these medication to provide required dose parameters Still further, the present subject matter renders an ability to increase number of doses that can be delivered by the device without changing the form factor.

Last but not the least, the present subject matter renders a dose counter which count each dose individually and provides visual indication for the remaining doses in the medication dispenser by incorporating for a priming/test dose correctly.

While specific language has been used to describe the disclosure, any limitations arising on account of the same are not intended. As would be apparent to a person in the art, various working modifications may be made to the method in order to implement the inventive concept as taught herein.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment.

The scope of embodiments is by no means limited by these specific examples. Numerous variations, whether explicitly given in the specification or not, such as differences in structure, dimension, and use of material, are possible.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

We claim:

1. A blister-strip based dispenser comprising:
    a base cover;
    a lever arm configured to be rotatable on receiving a user-actuation user actuation;
    a chassis for supporting placement of at least one blister-strip in a coil form of the coil, said blister-strip comprising medicament-pockets at at least one side of the blister-strip;
    a plurality of interconnected rollers connected from one end to the base cover by the lever arm comprising at least one roller linked to the lever arm and rotatable by the lever arm, said plurality of interconnected rollers configured for:
        anchoring the blister-strip from at one end for enabling a placement in the coil form and unwinding of the blister strip from the coil form;
        guiding at least two split-portions of the blister-strip;
        anchoring an end of each of said at least two split-portions of the blister-strip for winding the at least two split-portions separately; and
        anchoring an end of a lid-foil peeled off the at least two split-portions for winding the lid-foil; and
    a waste-dose collection mechanism to collect the non-inhaled medicament from the peeled blister-strip portions, wherein the waste-dose collection mechanism comprises:
    a plurality of gears different than the plurality of interconnected rollers, wherein the base cover is between the plurality of gears and the plurality of interconnected rollers;
    a plurality of open-ended funnels placed over the plurality of gears to collect a non-inhaled medicament upon alignment of the plurality of funnels with a plurality of slots in the gears.

2. The blister-strip based dispenser as claimed in claim 1, wherein the lever arm is pivoted within a housing of the dispenser for covering a mouthpiece in a closed state and exposing the mouthpiece in an open state, a transition from the closed state to the open state and vice versa configured to be triggered by the user actuation of the lever arm.

3. The blister-strip based dispenser as claimed in claim 1, wherein the chassis corresponds to an internal structure of a housing of the dispenser and comprises: a plurality of guide walls and a cavity for maintaining the blister-strip in the coil form.

4. The blister-strip based dispenser as claimed in claim 1, wherein the plurality of interconnected rollers are rotatable by a planetary gear system comprising a driving gear driven by the lever arm.

5. The blister-strip based dispenser as claimed in claim 4, wherein the planetary gear system comprises:
- a driving gear connected to the lever arm and supporting a lid-foil winding roller adapted for anchoring an end of the lid-foil and winding the lid-foil upon rotation;
- a set of driven gears by the driving gear for winding the at least two split-portions of the blister-strip and unwinding the blister-strip, said set of driven gears supporting one or more of:
- a roller adapted for anchoring the blister-strip from one end for enabling the placement in the coil form and for unwinding the blister strip from the coil form upon rotation; and
- a pair of the plurality of interconnected rollers defining a rotatable anchor spindle and adapted for anchoring the end of each of said at least two split-portions of the blister-strip for winding the at least two split-portions separately.

6. The blister-strip based dispenser as claimed in claim 1, wherein the plurality of interconnected rollers comprises a pair of roller guides for guiding and directing the at least two split-portions of the blister-strip to a corresponding roller of the plurality of interconnected rollers for winding the at least two split-portions separately.

7. The blister-strip based dispenser as claimed in claim 6, wherein the pair of roller guides are roller bearings for contacting the at least two split-portions of the blister strip and rotatable upon having been subjected to a drag generated by a movement of one of the at least two split-portions of the blister-strip towards its corresponding roller of the plurality of interconnected rollers.

8. The blister-strip based dispenser as claimed in claim 1, further comprising
- a chamber for storing the collected non-inhaled medicaments.

9. The blister-strip based dispenser as claimed in claim 1, wherein the blister-strip is a single blister strip folded at a center to exhibit said at least two split-portions.

10. The blister-strip based dispenser as claimed in claim 1, wherein the blister-strip based dispenser further comprises a dose counter mechanism comprising a driving gear and a driven gear arranged non-coaxially.

11. The blister-strip based dispenser as claimed in claim 9, wherein the driving gear comprises a slot for a unidirectional lock.

12. The blister-strip based dispenser as claimed in claim 10, wherein one complete rotation of the driving gear is adapted to rotate the driven gear to a quarter of the rotation of the driven gear.

* * * * *